United States Patent
Spillman, Jr. et al.

(10) Patent No.: US 6,170,488 B1
(45) Date of Patent: Jan. 9, 2001

(54) ACOUSTIC-BASED REMOTELY INTERROGATED DIAGNOSTIC IMPLANT DEVICE AND SYSTEM

(75) Inventors: William B. Spillman, Jr., Charlotte, VT (US); Eric M. Weissman, Chagrin Falls; Elmer D. Dickens, Jr., Richfield, both of OH (US)

(73) Assignee: The B. F. Goodrich Company, Brecksville, OH (US)

( * ) Notice: Under 35 U.S.C. 154(b), the term of this patent shall be extended for 0 days.

(21) Appl. No.: 09/275,311

(22) Filed: Mar. 24, 1999

(51) Int. Cl.[7] .................................................. A61B 19/00
(52) U.S. Cl. .......................................... 128/899; 128/903
(58) Field of Search ..................................... 128/897, 899, 128/903; 600/9, 12, 13, 407, 409, 437, 459, 463, 504, 505, 309; 623/1.1, 1.3, 11, 12; 607/61, 65, 60; 73/861.08, 861.18, 861.25, 861.26, 861.27

(56) References Cited

U.S. PATENT DOCUMENTS

| | | | |
|---|---|---|---|
| 4,114,606 | * | 9/1978 | Seylar .............................. 128/2.05 E |
| 4,227,407 | | 10/1980 | Drost .................................. 73/194 A |
| 4,352,960 | * | 10/1982 | Dormer et al. ............... 179/107 BC |
| 5,305,758 | | 4/1994 | Dietz et al. ..................... 128/662.06 |
| 5,306,644 | | 4/1994 | Myerholtz et al. .................. 436/149 |
| 5,358,514 | | 10/1994 | Schulman et al. ..................... 607/61 |
| 5,372,133 | | 12/1994 | Hogen Esch .......................... 128/631 |
| 5,411,551 | | 5/1995 | Winston et al. ......................... 623/1 |
| 5,620,475 | | 4/1997 | Magnusson ............................ 607/30 |
| 5,663,507 | | 9/1997 | Westervelt et al. .................... 73/727 |
| 5,709,225 | | 1/1998 | Budgifvars et al. ................. 128/899 |
| 5,720,771 | | 2/1998 | Snell ..................................... 607/60 |
| 5,735,887 | | 4/1998 | Barreras, Sr. et al. ................ 607/60 |
| 5,741,315 | | 4/1998 | Lee et al. ............................... 607/60 |
| 5,749,909 | * | 5/1998 | Schroeppel et al. ................... 607/33 |
| 5,891,180 | * | 4/1999 | Greeninger et al. .................. 607/32 |
| 5,967,986 | * | 10/1999 | Cimochowski et al. ............. 600/454 |
| 5,967,989 | * | 10/1999 | Cimochowski et al. ............. 600/459 |
| 5,972,029 | * | 10/1999 | Fuisz ...................................... 623/1 |
| 6,015,386 | * | 1/2000 | Kensey et al. ....................... 600/486 |
| 6,015,387 | * | 1/2000 | Schwartz et al. .................... 600/504 |

FOREIGN PATENT DOCUMENTS 9829030    7/1998   (WO).

OTHER PUBLICATIONS

"Sensing and Processing for Smart Structures"; W. B. Spillman, Jr.; Proceedings of the IEEE, vol. 84, No. 1, Jan. 1996 pp 68–77.

"Bio–Medical Telemetry Sensing and Transmitting Biological Information From Animals and Man"; R. Stuart Mackay; IEEE Press; (e g, pp 69–70 and pp298–315).

* cited by examiner

Primary Examiner—Cary O'Connor
Assistant Examiner—Charles Marmor, II
(74) Attorney, Agent, or Firm—Brian M. Kolkowski; Mark D. Saralino (57) ABSTRACT

A device and system for remotely interrogating a diagnostic implant device utilizes acoustic energy to power and/or interrogate the device. Acoustic energy is utilized to excite the device from outside the body of a patient. By analyzing the response of the device to such excitation, it is possible to ascertain the condition of the device. Additionally, acoustic energy may be used to provide operating power to the device.

22 Claims, 6 Drawing Sheets

ACOUSTIC-BASED REMOTELY INTERROGATED DIAGNOSTIC IMPLANT DEVICE AND SYSTEM

TECHNICAL FIELD

The present invention relates generally to medical implant devices, and more particularly to devices which may be interrogated remotely from outside the body.

BACKGROUND OF THE INVENTION

Various types of medical implant devices have been developed over the years. In many instances, such devices enable humans to live longer, more comfortable lives. Implant devices such as pacemakers, artificial joints, valves, grafts, stents, etc. provide a patient with the opportunity to lead a normal life even in the face of major heart, reconstructive, or other type surgery, for example.

It has been found, however, that the introduction of such implant devices can sometimes lead to complications. For example, the human body may reject the implant device which can ultimately lead to infection or other types of complications. Alternatively, the implant device may malfunction or become inoperative. Therefore, it is desirable to be able to monitor the condition of the implant device. On the other hand, it is highly undesirable to have to perform invasive surgery in order to evaluate the condition of the device.

Still further, it is desirable to be able to monitor conditions related to the use of implant devices. For example, in heart patients it may be helpful to know the amount of blood flowing through a stent or graft in order to evaluate the health of the patient. Again, however, it is undesirable to have to perform invasive surgery in order to evaluate such conditions.

Techniques have been developed which enable the function of an implant device to be monitored remotely from outside the body of the patient. These techniques involve including one or more sensors in the device for sensing the condition of the device. The device further includes a small transceiver for processing the output of the sensors and transmitting a signal based on the output. Such signal typically is a radio frequency signal which is received by a receiver from outside the body of the patient. The receiver then processes the signal in order to monitor the function of the device.

While such conventional techniques may be effective in avoiding the need to perform invasive surgery, there are however several drawbacks associated therewith. For example, the transceiver included in the implant device typically includes complex electrical circuitry such as mixers, amplifiers, microprocessors, etc. for receiving an interrogation signal and for transmitting a response signal based on the output of the sensors. Such complex circuitry has a relatively high cost associated therewith. In addition, the complexity of the circuitry increases the likelihood that the device itself may be defective. This would then require further invasive surgery and could even result in physical harm to the patient.

Still another shortcoming with conventional implant devices with sensors included therein is power concerns. Some type of circuit for providing power to the transceiver is necessary. The circuit may be a built-in power source such as a battery, or a circuit which derives operating power from an external excitation signal using magnetic or electromagnetic coupling. In either case, again the complexity of the circuit and/or the need to replace the battery periodically adds to the cost of the device and increases the opportunity for failure or defects.

In view of the aforementioned shortcomings associated with conventional implant devices, there is a strong need in the art for a medical implant device which can be remotely interrogated but which does not require complex electrical circuitry such as mixers, amplifiers, microprocessors, etc. There is a strong need for a medical implant device which carries out a function within a human or other living animal, and can be remotely interrogated simply and reliably. Moreover, there is a strong need for a medical implant device which does not rely on complex energy conversion circuits in order to operate.

SUMMARY OF THE INVENTION

The present invention is responsive to the aforementioned shortcomings with conventional devices, and is directed towards an implant device which includes a structure implantable within the living animal, and a sensor comprised in the structure and operatively configured to sense a biological parameter associated with the living animal. The sensor is responsive to acoustic waves provided from outside the living animal to produce an output indicative of the sensed biological parameter, with the structure being configured to transmit the output so that the output may be received from outside the living animal.

According to another aspect of the invention, a diagnostic system is provided. The system includes a structure implantable within a living animal and operatively configured to carry out or assist in carrying out a function within the living animal. The structure exhibits a mechanical transfer function which, in response to mechanical excitation, causes the structure to produce an acoustic signal having a characteristic which is modulated in relation to a parameter associated with the carrying out the function. The system further includes an exciter for acoustically transferring mechanical energy to the structure from outside the living animal, and a receiver located outside the living animal which detects the acoustic signal produced by the structure, processes the acoustic signal in relation to the mechanical transfer function, and provides an output indicative of the parameter based on the processed acoustic signal.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DESCRIPTION OF THE PREFERRED EMBODIMENTS

The present invention will now be described with reference to the drawings, wherein like reference numerals are used to refer to like elements throughout.

Figure 1:
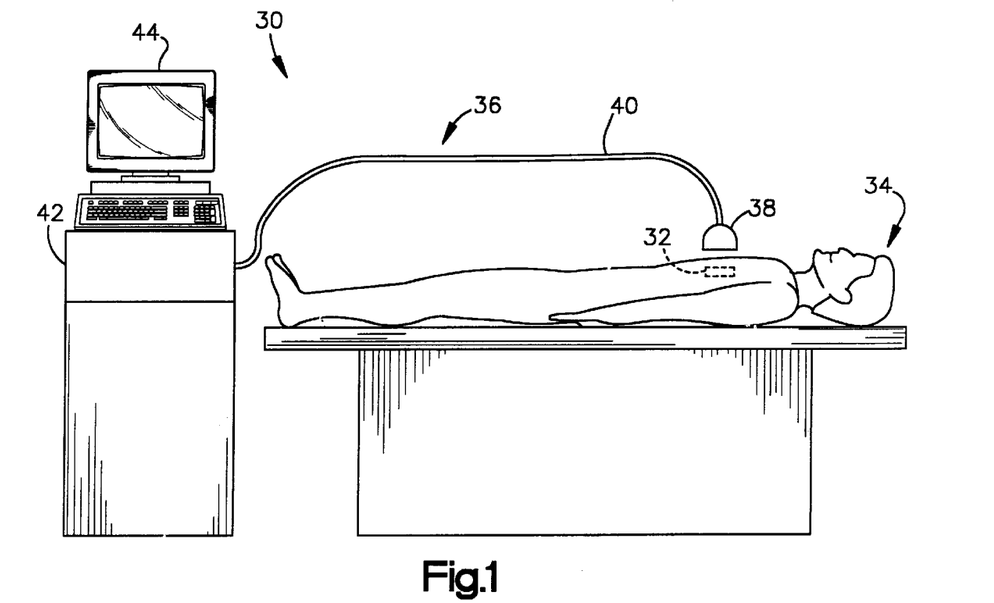
FIG. 1 is an environmental view illustrating a system including a remotely interrogated medical implant device and broadband acoustic analyzer in accordance with the present invention.

Referring initially to FIG. 1, a system for remotely interrogating a medical implant device according to the invention is generally designated 30. The system 30 includes a medical implant device 32 which is implanted in a living animal such as a human patient 34. As is discussed in more detail below, the medical implant device 32 can be any of a wide variety of different types of devices including, for example, a stent, graft, artificial joint, etc.

The device 32 preferably is configured to carry out or assist in carrying out a function within the patient 34. For example, in the case of a stent the device 32 prevents the closing of an arterial wall and permits the flow of blood therethrough. In the case of a graft, the device 32 serves to couple blood flow between two separate ends of a blood vessel. The device 32 may instead consist of an artificial hip or knee which facilitates movement of the leg of the patient 34. Other types of devices include, but are not limited to, a hemodialysis shunt and spinal brace, for example.

According to a series of embodiments described below in connection with FIGS. 13–18, the device 32 includes a sensor (not shown in FIG. 1) which serves to sense a parameter associated with the function performed by the device. For example, in the case of a stent or graft the sensor may be used to detect the degree of restenosis which occurs within the device 32. Alternatively, for example, the sensor may detect an amount of strain or displacement which occurs in an artificial hip or knee. Still further, the sensor may serve to sense the condition of the implant device in carrying out its intended function. For example, in the case of a pacemaker the sensor may detect the pulse rate.

The sensor, in such case, requires electrical power in order to operate. The present invention includes, in part, providing electrical energy to the device 32 by way of acoustic excitation. The device 32 includes a mechanism for converting acoustic energy provided from outside the body of the patient 34 into electrical energy which is stored for electrically driving the device 32.

According to still other embodiments of the invention as discussed more fully below in connection with FIGS. 3–12, the device 32 has a mechanical transfer function which is responsive to mechanical energy. The mechanical transfer function varies in a known manner relation to the condition of the implant device 32. By analyzing the response of the device 32 to acoustically provided mechanical energy, the present invention determines the condition or function of the device 32.

The system 30 further includes an acoustic analyzer 36 for remotely powering and/or interrogating the implant device 32 in order to evaluate the device function. The analyzer 36 in the exemplary embodiment includes a broadband acoustic source/detector unit 38 which is positioned outside the patient 34 in close proximity to the implant device 32. As will be discussed in more detail below, the source/detector unit 38 serves to excite the device 32 with acoustic energy. The acoustic energy in turn powers the device 32 and/or is used to evaluate the mechanical transfer function of the device 32. The source/detector unit 38 may then receive acoustic signals radiated by the device 32 in response to the excitation. Such signals can then be processed by the analyzer 36 to detect a parameter of interest (e.g., blood flow, amount of restenosis, etc.).

The source/detector unit 38 is coupled via an electrical cable 40 to the main circuitry 42 included in the analyzer 36. The main circuitry 42 includes suitable circuits for driving the source/detector unit 38 as described below, and for processing the output of the source/detector unit 38 in order to provide an output to an operator (e.g., display 44).

As will be better understood based on the description which follows, the present invention utilizes acoustic coupling between the source/detector unit 38 and the implant device 32. The device 32 is designed to respond to acoustic energy transmitted by the source/detector 38 in a manner which eliminates the need for complex electronics, power supplies, etc. within the device. In this manner, the device 32 can be a very simple, relatively low cost device which is less prone to failure. The device 32 does not require an active transmitter, mixer, amplifier, etc. as in other conventional devices. Moreover, the patient 34 is exposed to less high frequency radiation as compared to other types of remotely interrogated implant devices, thus improving the safety of the device.

Figure 2:
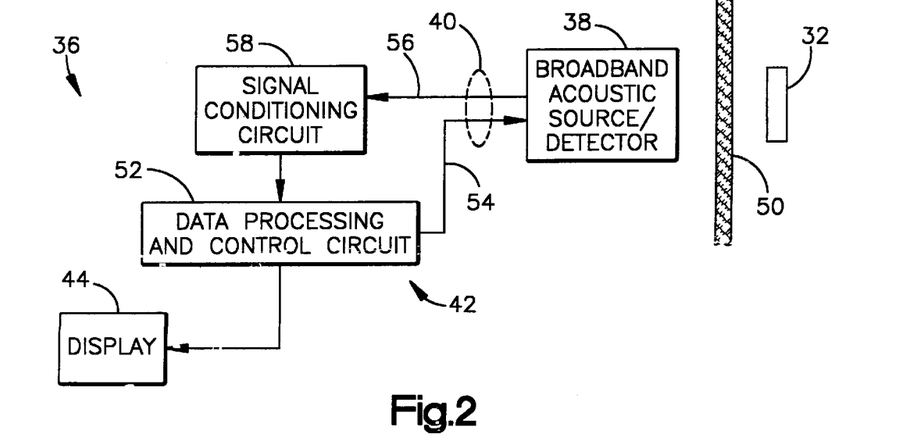
FIG. 2 is a block diagram of the broadband acoustic analyzer in accordance with the present invention.

Referring now to FIG. 2, the acoustic analyzer 36 in accordance with the exemplary embodiment is illustrated in more detail. The source/detector unit 38 preferably is a hand-held sized device which is held by a doctor, nurse or medical assistant outside the body of the patient 34 in close proximity to the implant device 32. Since the system 30 is non-invasive, the source/detector unit 38 may be placed adjacent the implant device 32 with the body of the patient (e.g., skin, muscle tissue, etc.), designated 50, disposed therebetween.

The analyzer 36 includes a data processing and control circuit 52 which is programmed to carry out the various control and computational functions described herein. More particularly, the circuit 52 provides a control signal on control bus 54. The control signal controls the frequency (within the acoustic frequency band) at which the source/detector 38 excites the device 32 by emitting acoustical energy while positioned in close proximity to the device 32 as shown. In addition, the control circuit 52 provides a control signal on bus 54 in order to control whether the source/detector 38 is transmitting acoustic energy or receiving acoustic energy reradiated from the device 32 in response to being excited.

The source/detector 38 receives acoustic energy transmitted from the device 32 and converts the energy into an electrical signal on line 56. The signal on line 56 is input to a signal conditioning circuit 58 which conditions the signal prior to being input to the control circuit 52. As is discussed more fully below, the control circuit 52 processes and analyzes the signal on line 56 in order to determine a parameter associated with the device. For example, the excitation signal from the source/detector 38 is used to induce a mechanical resonance in the device 32. The source/detector 38 then detects the response of the device 32 to such mechanical resonance by analyzing, for example, any harmonics which are present as determined by the acoustical energy radiated by the resonating device 32. Alternatively, the circuit 52 may analyze the decay time associated with the mechanical resonance in response to excitation by the source/detector 38.

Features such as the presence of harmonics and/or the decay time can be correlated to the function performed by the implant device. For example, the presence of harmonics in a stent 32 may increase or decrease as a function of the degree of restenosis which occurs within the stent. Thus, by monitoring the presence of harmonics over the course of periodic testing (e.g., trending), it is possible to track the build-up of restenosis. Similarly, the mechanical resonance decay time of the stent 32 may increase or decrease as a function of the amount of restenosis present in the stent. Still further, the system 30 can analyze changes in the mechanical resonance frequency itself and correlate such changes to the amount of restenosis. The scope of the present invention is intended to encompass any and all such correlations which may be found between the parameter of interest, the acoustic excitation and the response of the device.

Figure 3:
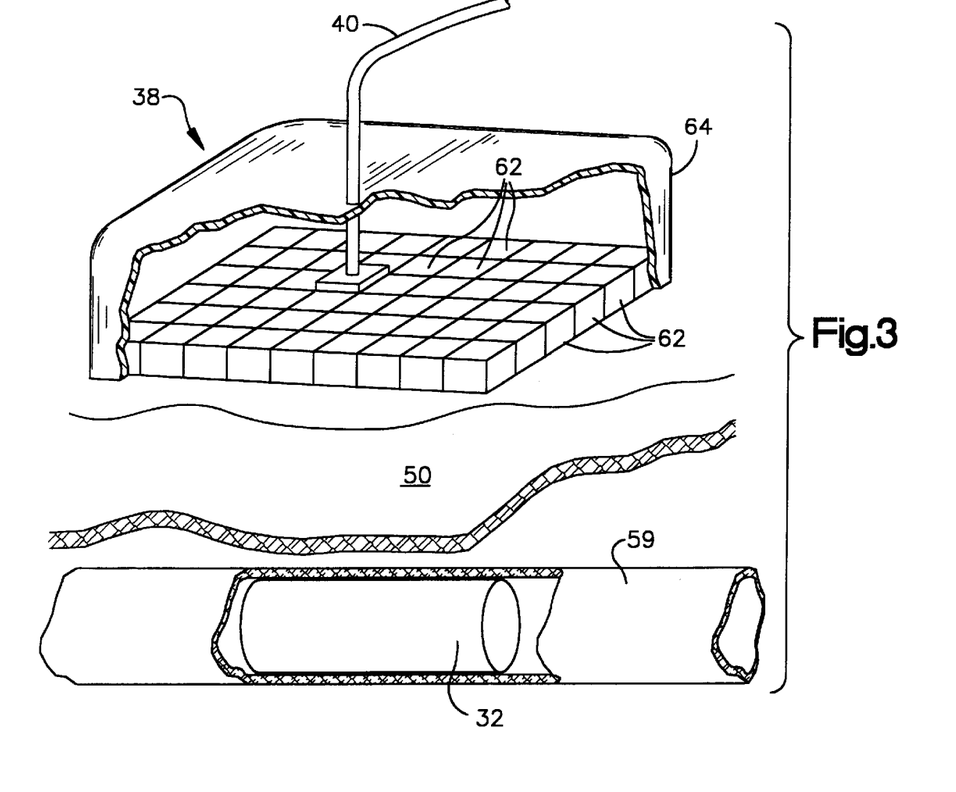
FIG. 3 is a partial schematic view representing an acoustic source/detector unit included as part of the acoustic analyzer, the source/detector unit being shown in physical proximity to an implant device being interrogated in accordance with the present invention.

FIG. 3 provides a perspective view of the source/detector 38 in relation to a stent type device 32 located in a blood vessel 59. As shown in FIG. 3, the source/detector 38 includes a two-dimensional (mxn) array 60 of miniature acoustic devices 62. Each device 62 is made up of an electro-acoustic transducer such as a piezoceramic device. In a transmit or excite mode, each device 62 is responsive to an electrical driving signal so as to emit an acoustic wave. Conversely, in a receive mode each device is designed to receive an acoustic wave and convert the received wave into an electrical signal. The level of the signal is based on the intensity of the received wave. Although the preferred embodiment utilizes an array 60 of piezoceramic devices 62, other type devices can also be used without departing from the scope of the invention.

The devices 62 are arranged in a generally planar array. The active faces of the devices 62 are oriented in a common direction so as to be directed downward towards the implant device 32. A housing 64 (shown in cut-away) provides a protective enclosure for the source/detector 38, with an acoustic window provided in the housing 64 to allow acoustic waves to be emitted and received by the devices 62.

Figure 4:
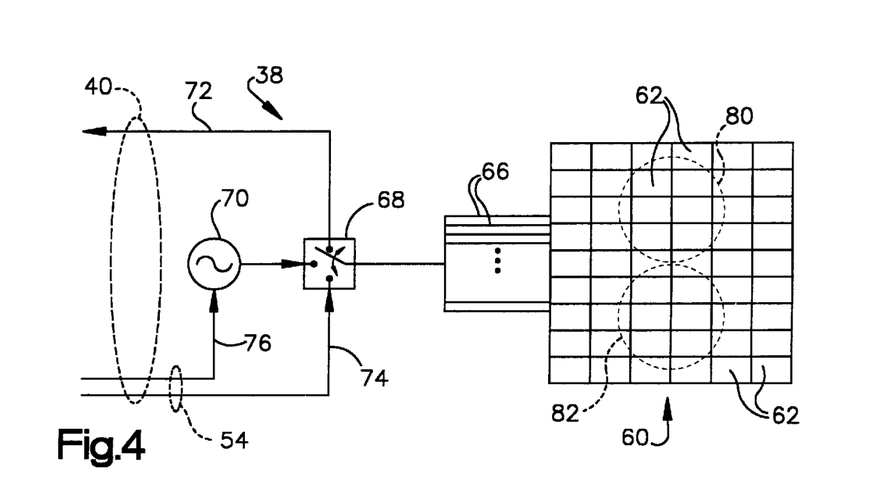
FIG. 4 is a block diagram of the source/detector unit in accordance with the present invention.

As is illustrated in FIG. 4, an electrical input/output 66 of each device 62 in the array 60 is hardwired together with the others in parallel. The input/outputs 66 are selectively connected via a switch 68 to either the output of a voltage controlled oscillator (VCO) 70 or a received signal line 72. During a transmit or excite mode, a control signal on line 74 from the control circuit 52 (FIG. 2) causes the switch 68 to couple the output of the oscillator 70 to the input/output 66 of each of the devices 62. At the same time, the control circuit 52 provides a control voltage on line 76 to control the frequency of the VCO 70.

Figure 5:
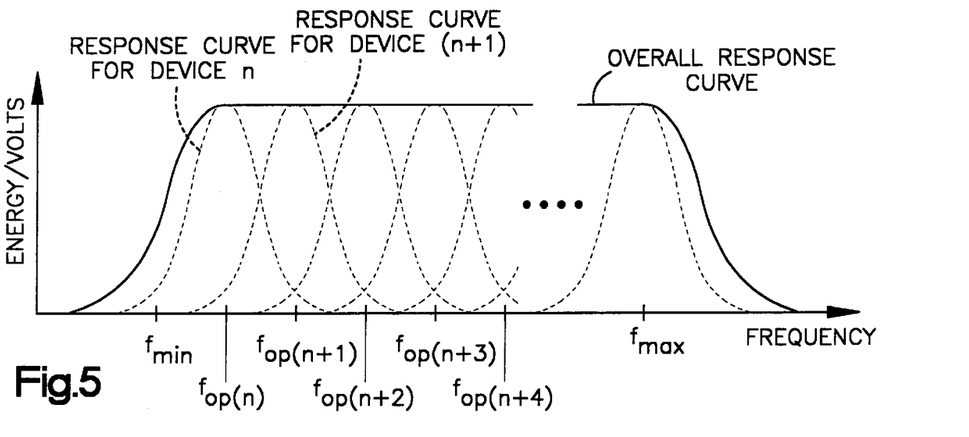
FIG. 5 is a block diagram of the broadband frequency response of the source/detector unit in accordance with the present invention.

The VCO 70 preferably is an oscillator which is designed to produce an output signal at any frequency within the acoustical range of 50 kilohertz (kHz) to 10 megahertz (MHz). Furthermore, it is desirable that each of the devices 62 provide a generally uniform response throughout the range. However, with existing piezoceramic devices 62 currently available, each device has a generally narrow band of operation (e.g., on the order of ±5% about its center operating frequency $f_{op}$). Consequently, the array 60 in the present invention is made up of devices 62 selected with different operating frequencies $f_{op}$ uniformly distributed across the broadband acoustical range of 50 kHz to 10 MHz. As a result, the composite response of the devices 62 is generally uniform as represented in FIG. 5.

In this manner, the array 60 is able to transmit and detect acoustic energy regardless of the particular frequency at which the device 32 is to be excited or at which the device 32 emits acoustic energy in response to excitation. The operating frequencies $f_{op}$ of the devices 62 are selected so that at least one device 62 is responsive to the excitation signal from the VCO 70 in order to emit an acoustic signal at each frequency. Similarly, at least one device 62 is responsive in the receive mode to detect the respective frequencies reradiated by the device 32, including any harmonics.

In a further preferred embodiment, the devices 62 with the different operating frequencies $f_{op}$ are spatially distributed within the array 60. Such spatial distribution preferably is selected so that the respective operating frequencies will be uniformly distributed across the array 60 and the overall frequency response of any region within the array 60 will be the same as the other. For example, regions 80 and 82 each preferably contain a sufficient number of devices 62 with selected operating frequencies to exhibit the same response curve shown in FIG. 5. Therefore, it will be appreciated that the overall array 60 will function as a broadband source/detector generally independent of the particular region (e.g., 80 or 82) which is positioned immediately adjacent the device 32. The array 60 therefore will be operative throughout the entire acoustic frequency band of interest.

Briefly referring back to FIG. 3, the stent device 32 may be a conventional stent which generally consists of a cylindrical tube. The tube may be made of metal such as stainless steel, or another material such as plastic and/or a composite material. The tube wall may be uniform, helical, or some other geometry.

Notably, the stent 32 inherently has physical mass and hence will have a mechanical resonance based upon its physical configuration and the material of which it is made. Such mechanical resonance will occur at its resonant frequency $\omega_R$ (or frequencies in the case of these being multiple mechanical resonances). The inventors have recognized that if the stent 32 is excited at its resonant frequency $\omega_R$ and the excitation is turned off, the stent 32 will reradiate acoustic energy at the resonant frequency $\omega_R$ and harmonics thereof, i.e., $2\omega_R$, $3\omega_R$, $4\omega_R$, etc. The reradiated signal will be damped by a factor of $e^{-at}$. By empirical study and/or modeling, it can be determined that the damping coefficient "a" will depend on the amount of restenosis present in the stent 32.

Figure 7:
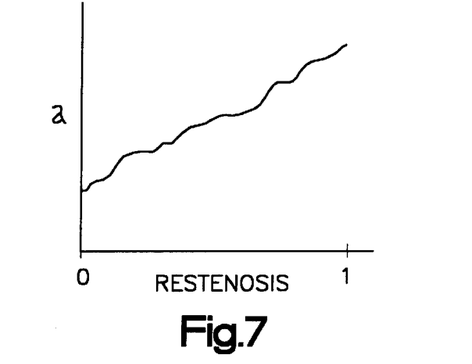
FIG. 7 is a graph illustrating a variation in damping constant of a stent as a function of degree of restenosis in accordance with the present invention.

FIG. 7 illustrates how the damping coefficient "a" varies with respect to degree of restenosis. In FIG. 7, a level 0 restenosis represents no occlusion in the stent and the damping coefficient "a" is at a local minimum. A level 1 restenosis represents complete occlusion at which the damping coefficient "a" is at a local maximum. Thus, the stent 32 can be said to have a mechanical transfer function which varies in relation to the degree of restenosis.

The amplitude distribution of the reradiated signal from the stent 32 in the frequency domain can be found from the Fourier transform of the reradiated signal. Moreover, it can be shown that the damping coefficient "a" is given by the following equation:

$$a = \frac{1}{2}\sqrt{\frac{P_1}{P_0 - P_1}}\,\omega_R \quad \text{(Equ. 1)}$$

where $P_0$ and $P_1$ represent power level at the resonant and first harmonic frequencies, respectively.

Thus, if a time series measurement of the reradiated acoustic energy from the stent 32 is made and then Fourier transformed so that the power at $\omega_R$ and $2\omega_R$ can be determined, then the damping coefficient "a" can be determined from Equ. 1 above. The amount of occlusion or degree of restenosis can then be estimated via the correlation represented in FIG. 7.

Figure 6:
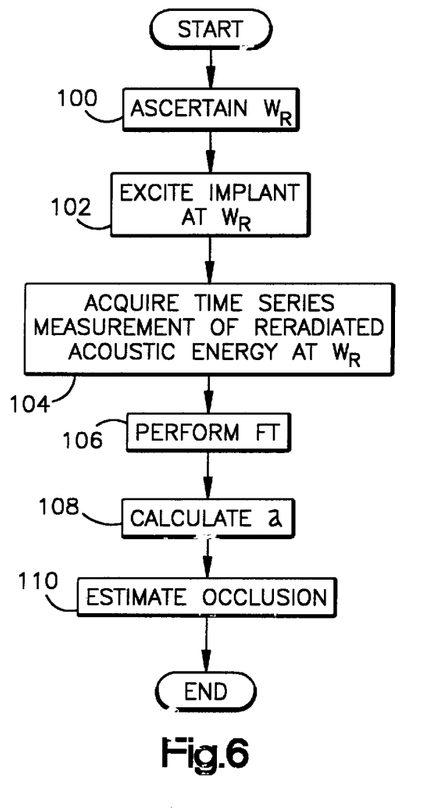
FIG. 6 is a flowchart illustrating steps for interrogating a stent to estimate restenosis according to one embodiment of the present invention.

FIG. 6 is a flowchart representing the above analysis as carried out by the system 30 in accordance with one embodiment of the invention. The data processing and control circuit 52 (FIG. 2) includes a microprocessor which is programmed to carry out the appropriate control and processing described herein. Such programming will be apparent to those having ordinary skill in the art based on the disclosure provided herein. Hence, further details regarding the particular programming have been omitted for sake of brevity.

Beginning in step 100, the system 30 initializes itself by ascertaining the most suitable resonant frequency $\omega_R$ of the stent 32. More particularly, the source/detector unit 38 is held in close proximity to the patient's body with the array 60 facing the stent 32 (e.g., as represented in FIG. 1). The control circuit 52 (FIG. 2) systematically begins to sweep the output frequency of the VCO 70 through the acoustic frequency band in which the resonant frequency $\omega_R$ is expected to appear. The output of the VCO 70 is applied to the array so that the stent 32 is excited by the acoustic energy at the frequency of the VCO 70. The control circuit 52 systematically samples the acoustic energy which is reradiated by the stent 32 at each frequency by controlling the switch 68. The energy level of the reradiated signal at each particular frequency is input to the control circuit 52 from the signal conditioning circuit 58.

Since the source/detector 38 is broadband as noted above, at least one device 62 is operative at each frequency to transmit and receive the acoustic signal. The control circuit 52, in step 100, determines at which frequency in the acoustic frequency band the reradiated acoustic energy is at its highest level as detected by the source/detector 38. Such maximum energy frequency level will correspond to the most suitable resonant frequency $\omega_R$ of the stent 32, typically, and thus the control circuit 52 ascertains the resonant frequency $\omega_R$.

Next, in step 102, the control circuit 52 causes the source/detector 38 to excite the stent 32 with a brief burst of acoustic energy at the resonant frequency $\omega_R$. Immediately following the brief burst, the control circuit 52 changes the position of the switch 68 so that the acoustic energy reradiated by the stent 32 in response to the excitation can be detected. The detected energy is input to the control circuit 52 from the conditioning circuit 58. The control circuit 52 then proceeds to take a time series measurement of the reradiated acoustic energy from the stent 32 as represented in step 104.

Next, the control circuit 52 takes the Fourier transform of the time series data in step 106. The Fourier transform yields, among other things, the energy components of the reradiated acoustic energy at the resonant frequency $\omega_R$ and the first harmonic. These values for $P_0$ and $P_1$, respectively, are then used by the control circuit 52 in step 108 to compute the damping coefficient "a" based on Equ. 1 above. The control circuit 52 then compares the value of the damping coefficient "a" with a table stored in memory representing the graph of FIG. 7, for example. Based on the value of "a", the control circuit 52 estimates the degree of restenosis as represented in step 110. The control circuit 52 may then provide an output on the display 44 or the like indicating such estimate. Moreover, the control circuit 52 may store such information in memory for future use in trending or the like.

In an alternate embodiment, the control circuit 52 may use other known data analysis techniques to analyze the frequency content of the acoustic energy reradiated from the stent 32. For example, wavelet transformations and/or neural network techniques may be employed by the control circuit. Moreover, such techniques may be modified to account for different conditions in taking the measurements such as large muscle mass, nearby bone structures, etc.

Additionally, the control circuit 52 may employ such techniques as pattern recognition to analyze the reradiated acoustic energy. For example, the control circuit 52 may be programmed to carry out pattern recognition to analyze the class of resonant frequencies exhibited by the stent 32 in response to the acoustic excitation.

Figure 8:
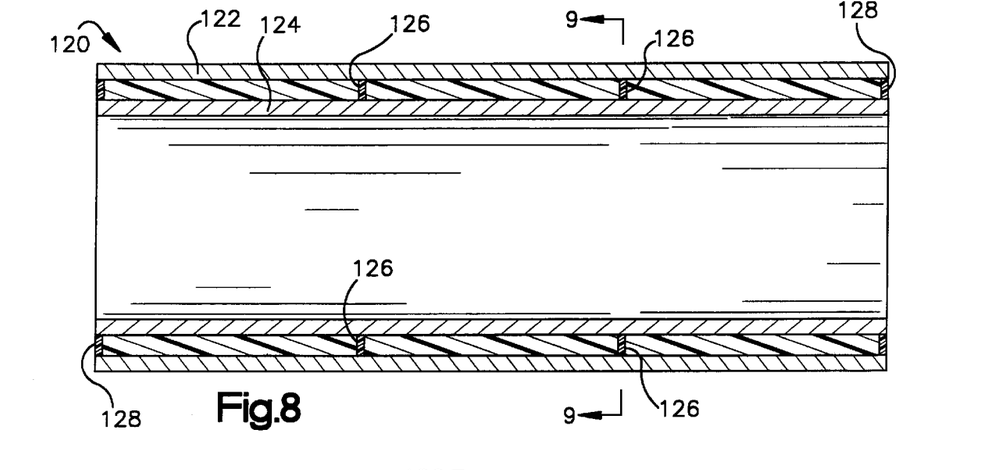
FIG. 8 is a cross-section view of a dual-cylinder stent in accordance with the present invention.
Figure 9:
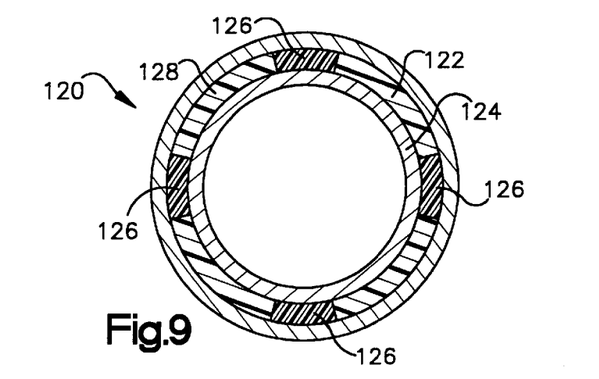
FIG. 9 is a cross-section view taken along line 9—9 of the stent in FIG. 8 in accordance with the present invention.

FIGS. 8 and 9 illustrate a specially designed acoustic reradiating stent 120 which can be substituted for the otherwise conventional stent 32 described above. The stent 120 is made up of two hollow concentric cylinders 122 and 124 which are mechanically connected so that the entire structure has a pronounced mechanical resonance at a resonant frequency $\omega_R$ within the acoustic frequency band. The outer cylinder 122 and the inner cylinder 124 are each made of a biocompatible material such as stainless steel, plastic, etc.

The outer cylinder 122 is mechanically connected to the inner cylinder 124 by resilient connecting members 126. The connecting members 126 are made of a resilient material such as rubber or plastic. Each member 126 is sufficiently rigid to maintain generally a physical separation between the two cylinders, yet is sufficiently resilient to allow for relative movement between the cylinders 122 and 124 at the resonant frequency $\omega_R$. In the exemplary embodiment, the connecting members 126 are equally spaced around the circumference of the cylinders. However, it will be appreciated that other configurations are also possible.

The stent 120 further includes a seal ring 128 at each end which seals off the circumferential area between the two cylinders 122. The seal rings 128 prevent blood from entering the area between the cylinders. The seal rings 128 are made up of a resilient material such as rubber or plastic similar to the connecting members 128.

Hence, the stent 120 will exhibit a pronounced mechanical resonance based on the relative motion which can occur between the two concentric cylinders.

The stent 120 may be utilized in accordance with the system 30 as described in relation to FIG. 6. In particular, the damping coefficient may be calculated based on the harmonic ratio and used to estimate occlusion as described above. In an alternative embodiment, however, the degree of restenosis may be estimated using a different, albeit related, criteria.

Figure 10:
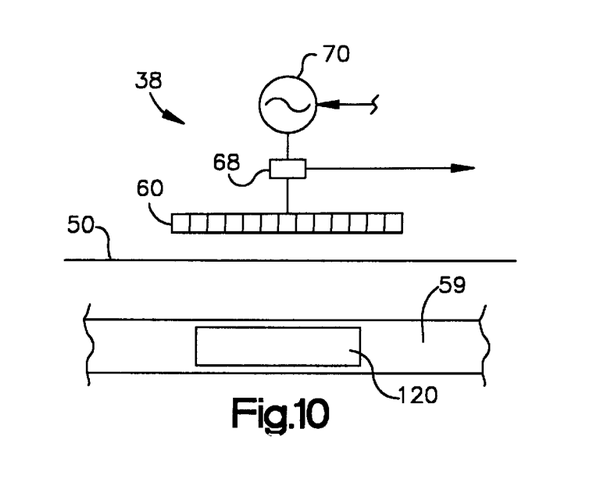
FIG. 10 is schematic view representing an acoustic source/detector and the stent of FIGS. 8 and 9 in accordance with the present invention.
Figure 11:
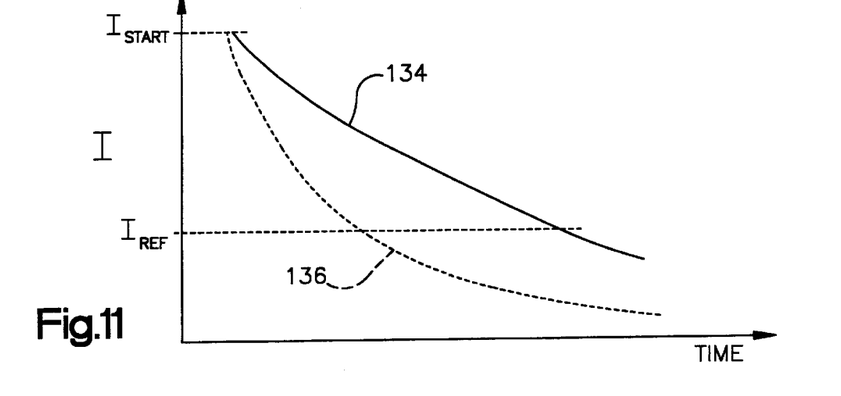
FIG. 11 is a graph illustrating a change in resonance decay time as a function of degree of restenosis in accordance with the present invention.

For example, FIG. 10 illustrates represents a configuration of the system 30 in which the decay time of the reradiated acoustic energy is utilized to estimate restenosis. More particularly, the stent 120 is excited at its resonant frequency $\omega_R$ in a manner similar to that described above in steps 100 and 102 in FIG. 6. Upon switching the switch 68 from excite mode to receive mode, the array 60 is then used by the control circuit 52 to detect the acoustic energy reradiated from the stent 120 at the resonant frequency $\omega_R$. In this particular embodiment, the control circuit 52 filters out any harmonics received from the source/detector 38 using a Fourier transform or adjustable filter, for example, and concentrates on the acoustic energy received at the resonant frequency $\omega_R$.

Figure 12A:
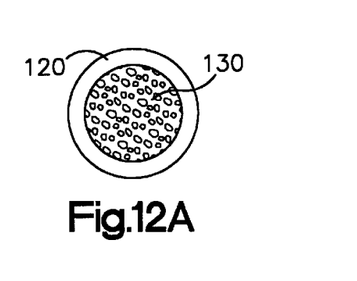
FIG. 12a and 12b are cross-section views illustrating a stent with different degrees of restenosis.
Figure 12B:
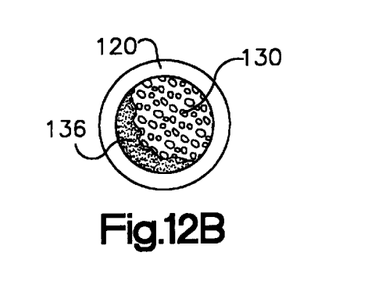

Specifically, the control circuit 52 measures the amplitude of the reradiated acoustic energy over time in order to determine the decay time of the mechanical resonance. With no restenosis, the cross section of the stent 120 will be filled with blood 130 as represented in FIG. 12a. The non-occluded stent 120 will have a characteristic acoustic reradiation frequency and decay time following excitation as represented by curve 134 in FIG. 11. As restenosis proceeds, the non-blood tissue 136 will begin to fill the cross section of the stent 120 as shown in FIG. 12b. Depending on the particular design of the stent 120, the restenosis build-up will modify either the decay time of the reradiated acoustic energy, the resonant frequency $\omega_R$, or both.

In the exemplary embodiment, the stent 120 varies in decay time as a function of increasing restenosis. Thus, the decay time may decrease as restenosis increases as represented by curve 136 in FIG. 11. By comparing the decay time of the reradiated acoustic energy from a given energy level $I_{start}$ to a second level $I_{ref}$, the control circuit 52 is programmed to estimate the degree of restenosis. Such estimate can be based on expected values stored in the circuit 52. In addition, or in the alternative, the measured decay time can be stored in memory in the circuit 52 for purposes of trending.

It will be appreciated that several inventive aspects have been described herein with respect to a stent 32 or 120. Nevertheless, it will be further appreciated that the same inventive aspects apply to other medical implant devices such as grafts, joints, etc. While analyzing the acoustic energy reradiated by the device is described in connection with determining the amount of restenosis, it will be appreciated that other parameters may also be determined. For example, the ratio of the harmonic content, variations in the decay time, resonant frequency $\omega_R$, etc., can be utilized by the control circuit 52 to estimate stress, strain, etc., within the device. Provided the mechanical transfer function of the device 32 can be determined in relation to a parameter of interest, the present invention allows such information to be obtained remotely from the implanted device using acoustic energy.

Figure 13:
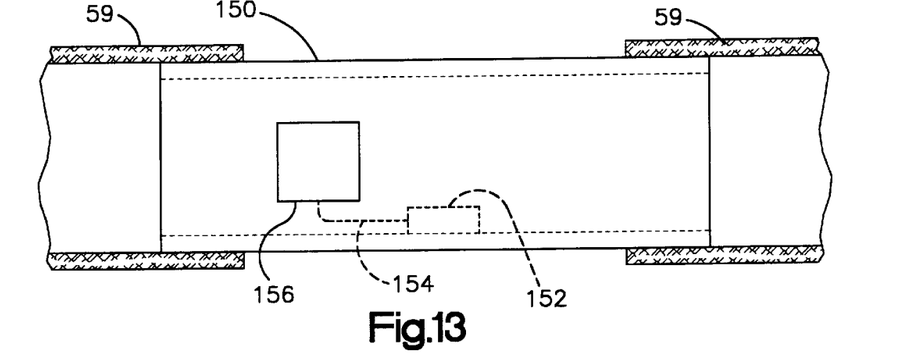
FIG. 13 is a schematic view of an acoustically powered graft in accordance with another embodiment of the invention.

FIG. 13 illustrates another aspect of the invention whereby the acoustic energy from the source/detector 38 is used to provide operating power to an implant device. For example, FIG. 13 illustrates a graft 150 in accordance with the present invention. The graft 150 is tube shaped and is surgically inserted between two ends of a blood vessel 59 as is conventional. As is known, the graft 150 serves to permit blood flow between the respective ends of the vessel 59. The body of the graft 150 may be made of metal, plastic, a composite material, etc.

The graft 150 includes a sensor 152 which is mounted, for example, on an inner wall of the tube as shown in FIG. 13. The sensor 152 may be of a type designed to provide an impedance which varies as a function of the rate of bloodflow through the vessel, the amount of restenosis, the oxygen level within the blood therein, etc. The sensor 152 is connected by way of wires 154 to a main circuit 156 formed within a sealed housing and mounted to an outer wall of the tube, for example.

Figure 14:
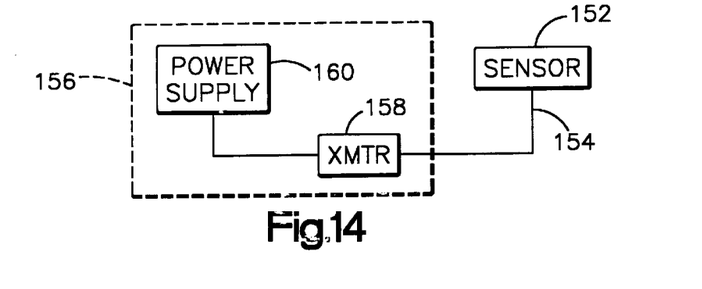
FIG. 14 is an electrical block diagram of the graft in FIG. 13 in accordance with the present invention.

As shown in FIG. 14, the main circuit 156 includes a miniature transmitter 158 and a power supply 160. The transmitter 158 is designed to transmit a signal which is encoded with information based on the parameter sensed by the sensor 152. As is described below in connection with FIGS. 17 and 18, the transmitted signal may be an electromagnetic signal, magnetic signal, or an acoustic signal, for example. The power supply 160 provides operating power to the transmitter 158 and/or the sensor 152, as needed.

Figure 15:
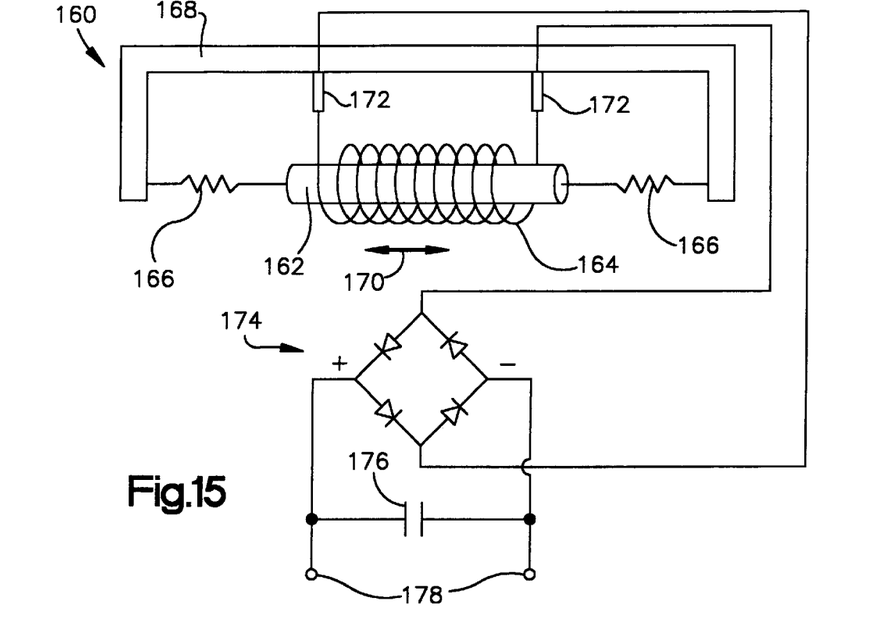
FIG. 15 is schematic diagram of acoustically driven power source in accordance with the present invention.

FIG. 15 illustrates in detail the configuration of the power supply 160 in accordance with the exemplary embodiment. The power supply 160 includes a cylindrical permanent magnet 162 oriented as a core within a miniature coil 164. The power supply 160 further includes spring members 166 attached between respective ends the core 162 and a support frame 168. The spring members 166 allow the core 162 to move laterally relative to the axis of the coil 164 in an oscillating manner as represented by arrow 170.

Movement of the core 162 relative to the coil 164 induces a current in the coil 164. Such induced current is output through coil terminals 172 and is input to a diode rectifier circuit 174 included in the power supply 160. The output terminals of the rectifier circuit 174 are coupled across a capacitor 176 so that the energy of the induced current is stored as charge across the capacitor 176. The output terminals 178 across the capacitor 176 are coupled to the transmitter 158 to provide the appropriate operating power.

As previously mentioned, the core 162 is mechanically arranged so that it is moveable relative to the coil 164. More particularly, the core 162 and spring elements 166 are selected in order that there is some resonance frequency in the acoustic range at which small perturbation forces will produce large non-linear displacements of the core 162 relative to the coil 164. The source/detector 38 of the system 30 may then be used to provide acoustic energy to the core 162 from outside the body of the patient. The acoustic energy induces relative motion between the core 162 and the coil 164 such that a current is induced within the coil 164 itself. The current is then rectified and stored in the capacitor 176. In this manner, the power supply of the implant device 150 can be recharged using acoustic energy provided from outside the body.

Figure 16:
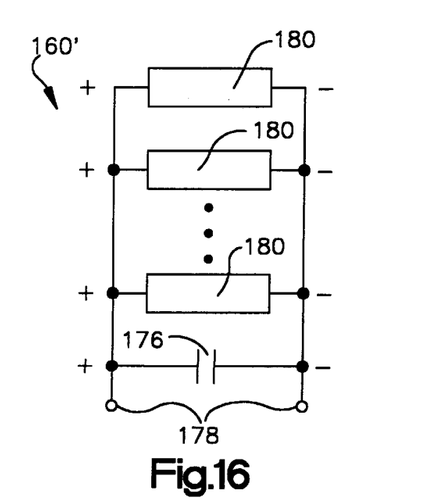
FIG. 16 is a schematic diagram of an acoustically driven power source in accordance with another embodiment of the present invention.

FIG. 16 illustrates an alternative embodiment of the power supply 160, in this case designated 160'. In this particular embodiment, the power supply 160' includes a plurality of elements 180 connected in parallel. Each element 180 includes a core 162, coil 164 and rectifier circuit 174 configuration similar to that shown in FIG. 15. The respective positive and negative outputs of the rectifier circuit 174 in each element 180 are connected in parallel and coupled to the storage capacitor 176. In this manner, the currents induced in each coil 164 for each element 180 are summed together to produce a total charge which is stored in the capacitor 176.

In the preferred embodiment, the spatial orientation of the coils 164 in each element 180 is different. Consequently, when the power supply 160' is excited by an acoustic signal (e.g., from source/detector 38) at the resonant frequency, the orientation of the array of elements 180 relative to the excitation signal will minimally affect the power output of the supply 160'.

Figure 17:
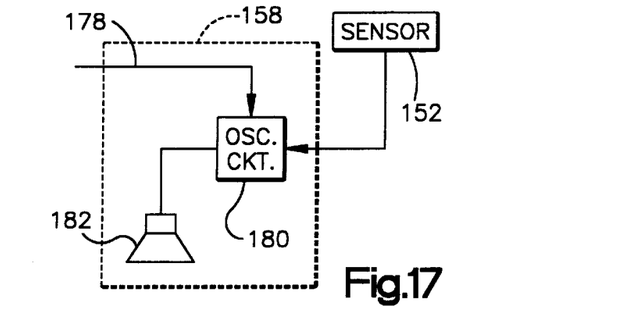
FIG. 17 is a block diagram of a transmitter in accordance with one embodiment of the present invention.
Figure 18:
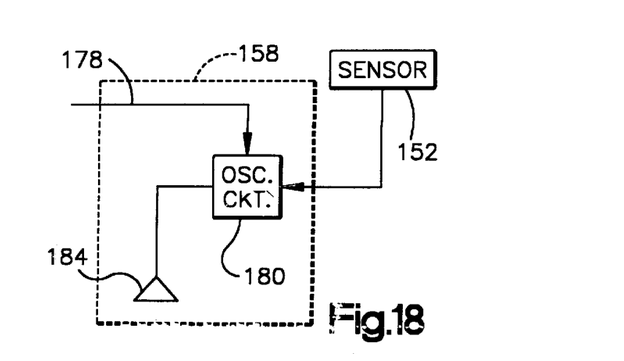
FIG. 18 is a block diagram of a transmitter in accordance with another embodiment of the present invention.

FIGS. 17 and 18 illustrate exemplary embodiments of the transmitter 158 in accordance with the invention. FIG. 17 represents an acoustic embodiment in which the transmitter 158 transmits an acoustic signal whose frequency varies based on a sensed parameter. For example, the transmitter 158 includes an oscillator circuit 180 which produces an output signal having a frequency within the acoustic frequency range and which varies as a function of the impedance presented by the sensor 152. The transmitter 158 further includes a piezoelectric element 182 which converts the electrical signal output from the oscillator 180 into an acoustic signal which in turn is transmitted through the body of the patient. The source/detector 38 in turn may be used to detect the acoustic signal transmitted by the element 182. By analyzing the frequency of the detected signal, the sensed parameter may be ascertained.

In the embodiment of FIG. 18, the oscillator circuit 180 is designed to produce an output signal in the radio frequency band. The frequency of the output signal again is varied based on the output of the sensor 152. The output signal is coupled to an antenna 184 which is used to transmit the signal to a receiver located outside the body of the patient. Again by analyzing the frequency of the detected signal, the sensed parameter may be ascertained.

Accordingly, the present invention provides a system by which operating power for a medical implant device may be provided simply and externally via acoustic energy. While the invention is described in the context of a graft 150, it will be appreciated that a wide variety of other types of implant devices may be substituted instead yet still remain within the intended scope of the invention.

While a moveable coil/core arrangement is described in connection with the embodiment of FIG. 15, it will be appreciated that other mechanisms are available for converting the acoustic energy provided from outside the body into electrical energy. For example, a piezoelectric transducer may be utilized in place of the coil/core arrangement.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. An implant device to be implanted within a living animal, comprising:

a structure implantable within the living animal; and a sensor comprised in the structure and operatively configured to sense at least one biological parameter associated with the living animal, wherein the sensor is responsive to acoustic waves provided from outside the living animal to produce an output indicative of the sensed at least one biological parameter, the structure being configured to transmit the output so that the output may be received from outside the living animal.

2. The implant device of claim 1, wherein the structure transmits the output as an acoustic wave.

3. The implant device of claim 1, wherein the structure transmits the output as an electromagnetic wave.

4. The implant device of claim 1, wherein the device operates on power derived from the acoustic waves.

5. The implant device of claim 4, wherein the structure includes at least one coil, and a magnetic core operatively arranged to engage in relative motion through the coil in response to the acoustic waves to generate electrical energy based upon which the device operates.

6. The implant device of claim 5, wherein the structure includes an array of coils with corresponding magnetic cores.

7. The implant device of claim 4, wherein the structure includes a transducer for converting the acoustic waves into electrical energy which drives the sensor.

8. The implant device of claim 7, wherein the output is an electromagnetic signal generated by the sensor in response to being driven.

9. The implant device of claim 1, wherein the structure comprises a stent.

10. The implant device of claim 1, wherein the structure comprises a graft.

11. A diagnostic system, comprising:

a structure implantable within a living animal and operatively configured to carry out or assist in carrying out a function within the living animal, the structure exhibiting a mechanical transfer function which, in response to mechanical excitation, causes the structure to produce an acoustic signal having a characteristic which is modulated in relation to a parameter associated with the carrying out the function;

an exciter for acoustically transferring mechanical energy to the structure from outside the living animal; and a receiver located outside the living animal which detects the acoustic signal produced by the structure, processes the acoustic signal in relation to the mechanical transfer function, and provides an output indicative of the parameter based on the processed acoustic signal.

12. The system of claim 11, wherein the structure comprises a stent.

13. The system of claim 12, wherein the mechanical transfer function of the stent varies in relation to restenosis occurring within the stent.

14. The system of claim 13, wherein the receiver detects harmonics within the acoustic signal and provides an output indicative of a degree of restenosis based on the detected harmonics.

15. The system of claim 11, wherein the structure comprises a graft.

16. The system of claim 11, wherein the exciter and receiver comprise a common array of transducers.

17. The system of claim 16, wherein respective transducers within the array are operative at different frequencies within a frequency range to provide broadband operation.

18. The system of claim 11, wherein the structure comprises a graft including two concentric cylinders.

19. The system of claim 18, wherein the graft further comprises resilient coupling members for coupling together the concentric cylinders.

20. The system of claim 11, wherein the receiver utilizes at least one of a Fourier transform, wavelet analysis, and neural network analysis to process the acoustic signal.

21. The system of claim 11, wherein the receiver evaluates frequency content of the acoustic signal in order to provide the output.

22. The system of claim 11, wherein the receiver evaluates a decay time of the acoustic signal in order to provide the output.

* * * * *